(12) United States Patent
Fan et al.

(10) Patent No.: US 11,801,236 B2
(45) Date of Patent: Oct. 31, 2023

(54) PRAMIPEXOLE HYDROCHLORIDE ORAL LIQUID

(71) Applicants: CHANGZHOU NO.4 PHARMACEUTICAL FACTORY CO. LTD, Changzhou (CN); BEIJING DO-PHARMA TECH CO. LTD, Beijing (CN)

(72) Inventors: Xinhua Fan, Changzhou (CN); Yanyuan Zhang, Beijing (CN); Yun He, Changzhou (CN); Pengfei Li, Beijing (CN); Xiang Zhang, Changzhou (CN); Longhao Wu, Beijing (CN); Peng Peng, Changzhou (CN); Sujing Zhuang, Changzhou (CN); Li Xiao, Beijing (CN); Yongrui Tu, Changzhou (CN)

(73) Assignees: CHANGZHOU NO.4 PHARMACEUTICAL FACTORY CO. LTD, Changzhou (CN); BEIJING DO-PHARMA TECH CO. LTD, Beijing (CN)

( * ) Notice: Subject to any disclaimer, the term of this patent is extended or adjusted under 35 U.S.C. 154(b) by 53 days.

(21) Appl. No.: 17/799,950

(22) PCT Filed: Jan. 8, 2021

(86) PCT No.: PCT/CN2021/070732
§ 371 (c)(1),
(2) Date: Aug. 16, 2022

(87) PCT Pub. No.: WO2021/238232
PCT Pub. Date: Dec. 2, 2021

(65) Prior Publication Data
US 2023/0061159 A1 Mar. 2, 2023

(30) Foreign Application Priority Data
May 23, 2020 (CN) .......................... 202010445120.8

(51) Int. Cl.
*A61K 31/428* (2006.01)
*A61K 9/00* (2006.01)
*A61K 9/08* (2006.01)

(52) U.S. Cl.
CPC ............ *A61K 31/428* (2013.01); *A61K 9/0053* (2013.01); *A61K 9/08* (2013.01)

(58) Field of Classification Search
CPC ....... A61K 31/428; A61K 9/0053; A61K 9/08; A61K 47/02; A61P 25/16
See application file for complete search history.

(56) References Cited

U.S. PATENT DOCUMENTS

2004/0266794 A1 12/2004 Mierau et al.

FOREIGN PATENT DOCUMENTS

| CN | 102846541 A | 1/2013 | |
|---|---|---|---|
| EP | 2870965 A1* | 5/2015 | ............... A61K 31/428 |

OTHER PUBLICATIONS

First Search Report issued in Chinese Application No. 202010445120.8; mailed Oct. 15, 2021; 2 pg.
International Search Report issued in International Application No. PCT/CN2021/070732; mailed Apr. 8, 2021; 7 pgs.

* cited by examiner

*Primary Examiner* — Joseph R Kosack
*Assistant Examiner* — David M Shim
(74) *Attorney, Agent, or Firm* — HAUPTMAN HAM, LLP

(57) ABSTRACT

The present invention provides a method for improving the stability of pramipexole or its salt preparation, and further provides a pramipexole hydrochloride oral liquid with excellent stability and oral absorption effect. The pramipexole hydrochloride oral liquid of the present invention is prepared through a simple process, and shows bioequivalence with the tablet containing pramipexole hydrochloride. The invention perfectly realizes multi-dose administration of pramipexole hydrochloride and improves the compliance and accessibility of medication for patients.

3 Claims, 1 Drawing Sheet

PRAMIPEXOLE HYDROCHLORIDE ORAL LIQUID

CROSS REFERENCE OF RELATED APPLICATION

This is a U.S. National Stage under 35 U.S.C 371 of the International Application PCT/CN2021/070732, filed Jan. 8, 2021, which claims priority under 35 U.S.C. 119(a-d) to CN 202010445120.8, filed May 23, 2020.

BACKGROUND OF THE PRESENT INVENTION

Field of Invention

The present invention provides preparations of pramipexole or pharmaceutical salts thereof, and preferably provides pramipexole hydrochloride oral liquid. It belongs to the field of pharmaceutical preparations.

Description of Related Arts

Parkinson's disease is a common, slowly progressing neurodegenerative disease that occurs in middle-aged and elderly people, and most of the patients develop the disease after 60 years of age. The main manifestations are slow movements of the patient, tremors of hands, feet or other parts of the body, and the body loses its original flexibility and coordination. At present, there is no complete cure for the disease, and long-term, continuous drug treatment is needed to inhibit the progression of the disease. Therefore, for such patients, a drug that is easy to take and has low side effects, stable curative effect, good tolerability and compliance is needed. Pramipexole can be used alone in the treatment of Parkinson's disease to reduce the incidence of dyskinesias caused by levodopa treatment. Combined with levodopa, it can reduce the dose and adverse effects of levodopa. Early use of pramipexole can delay the onset of these symptoms and improve the patient's quality of life.

Pramipexole, chemical name (S)-2-amino-4,5,6,7-tetrahydro-6-propylamine-benzothiazole, is an antihistamine and is mainly used clinically to treat Parkinson's Disease and its syndromes. Pramipexole hydrochloride refers to the monohydrate of pramipexole containing two hydrochloric acid molecules, the chemical formula is $C_{10}H_{17}N_3S \cdot 2HCl \cdot H_2O$, and the molecular weight is 211.32. Currently marketed dosage forms include immediate-release tablets and sustained-release tablets, of which the market specifications of immediate-release tablets are: 0.125 mg, 0.25 mg, 0.5 mg, 1.0 mg and 1.5 mg, and the tablets are packaged in aluminum. The pramipexole dihydrochloride monohydrate tablets marketed in the United States in 2005 have the problem of instability in storage. After 18 months of storage, there is only about 95% of the active ingredients in the average labeled amount of active ingredients. The curative effect and safety of the medicine are affected for patients.

At present, most of the commercially available pramipexole hydrochloride drugs are solid preparations, and these preparations are acceptable for therapeutic purposes. However, because the drug is aimed at elderly patients and the solid preparation is difficult for elderly patients to swallow, the use of solid preparations has increased serious compliance problems in such patients.

The stability of pramipexole or its pharmaceutically acceptable salts, such as pramipexole hydrochloride, especially in solution, limits the development of its preparations, especially preparations for elderly patients with dysphagia.

CN102846541A discloses a pramipexole oral liquid containing a buffer and its method. It is believed that controlling the pH range of the oral liquid has a great influence on the stability of the preparation. This document does not record the determination method of related substances in the stability influencing factor test. In addition, the inventors of the present invention conducted a stability influencing factor test on the pramipexole oral liquid containing citrate-sodium citrate buffer solution as the buffer which is the preferred embodiment in CN102846541A, and the results show the stability of the oral liquid is still not good and needs to be improved.

SUMMARY OF THE PRESENT INVENTION

In order to solve the problem of instability in storage of pramipexole or its pharmaceutical salt preparations, especially solution preparations, the inventors of the present invention surprisingly found a method to improve the stability of pramipexole or its pharmaceutical salt preparations. Therefore, the present invention provides a pramipexole or its salt preparation for storing stable, especially a new pramipexole hydrochloride oral liquid.

The technical scheme of the present invention is as follows:

The present invention provides a method for improving the stability of pramipexole or its salt preparation, characterized in that the preparation does not contain a buffer and/or a buffer system.

The method described above, preferably, the pramipexole or its salt is pramipexole hydrochloride.

Preferably, wherein the method described above, the preparation is a solution dosage form, for example, an oral liquid or an injection; more preferably, the preparation is an oral liquid.

As another object of the present invention, there is also provided a pramipexole hydrochloride oral liquid, which comprises pramipexole hydrochloride, a preservative and water, characterized in that the oral liquid does not contain a buffer or a buffer system.

Preferably, the pramipexole hydrochloride oral liquid described above, wherein the preservative may be paraben or its salt, benzoic acid or its salt, sorbic acid or its salt.

More preferably, the aforementioned pramipexole hydrochloride oral liquid, wherein the preservative comprises at least one member selected from a group consisting of methyl paraben, propyl paraben, ethyl paraben, butyl paraben, sodium methyl ester, sodium ethyl paraben, sodium propyl paraben, sodium butyl paraben, benzoic acid, sodium benzoate, sorbic acid, potassium sorbate; more preferably, The preservative mentioned is methyl paraben and/or propyl paraben.

Preferably, the aforementioned pramipexole hydrochloride oral liquid is characterized in that it further contains a chelating agent; preferably, the chelating agent comprises at least one member selected from a group consisting of aminotriacetic acid, hydroxyethylethylenediaminetriacetic acid, diethylenetriacetic acid, aminepentaacetic acid, ethylenediaminetetraacetic acid, disodium ethylenediaminetetraacetic acid (EDTA-2Na), and calcium disodium ethylenediaminetetraacetate (EDTA-CaNa2).

If necessary, the pramipexole hydrochloride oral liquid described above in the present invention may also contain a flavoring agent, which usually refers to a sweetener or a flavor.

The sweetener can be selected from one or more of sucrose, xylitol, sorbitol, fructose, glucose, aspartame, sucralose, acesulfame K, and sodium saccharin, for example, sucralose is preferred.

Flavors usually refer to fruit flavors, which can be selected from one or more of strawberry flavor, orange flavor, lychee flavor, mixed berry flavor, banana flavor, orange flavor, grape flavor, lime flavor, etc., for example, preferably blended with berry flavor.

In the above-mentioned pramipexole hydrochloride oral liquid of the present invention, the content of pramipexole hydrochloride per unit of preparation is 0.01 mg/ml-10 mg/ml; preferably, the content of pramipexole hydrochloride per unit of preparation is 0.02 mg /ml-1.0 mg/ml; preferably, the content of pramipexole hydrochloride per unit of preparation is 0.05 mg/ml-0.3 mg/ml; as a specific embodiment of the present invention, the pramipexole hydrochloride orally liquid described above, more preferably, wherein the content of pramipexole hydrochloride per unit of preparation is 0.125 mg/ml -0.25 mg/ml.

The pramipexole or its salt preparations of the present invention, especially pramipexole hydrochloride oral liquid, do not contain buffers and/or buffer systems, which show excellent stability and bioavailability. Buffers, also known as acid-base stabilizers, are generally salts, such as strong acid and weak base salts or weak acid and strong base salts, which gradually release the acid or base in the salt during reaction or storage to maintain a stable pH; The buffer system is generally a mixture of weak acids or weak bases and their salts. The buffer or buffer system in the present invention refers to a commonly used or conventional buffer or buffer system in the pharmaceutical field, and is not particularly limited, for example, including but not limited to citric acid-disodium hydrogen phosphate buffer solution, citrate-sodium citrate buffer solution, sodium dihydrogen phosphate-sodium hydroxide buffer solution, tartaric acid-sodium hydroxide, phosphate buffer solution, etc.

In the above-mentioned pramipexole hydrochloride oral liquid of the present invention, the content or dosage of preservatives, chelating agents, and flavoring agents can be used according to requirements in accordance with conventional dosages in the art, and there is no particular limitation. For example, in the pramipexole hydrochloride oral liquid, per unit preparation or per unit dose, the preservative content is usually 0.02% to 0.5% (w/v); the chelating agent usually contains 0.01-0.25% (w/v) ), the content of flavoring agent is 0.01-60% (w/v). Preferably, the preservative content can be 0.02% to 0.2% (w/v), the chelating agent content can be 0.01 to 0.05% (w/v), and the flavoring agent content can be 0.1-10% (w/v).

The present invention surprisingly found that without a buffer and/or buffer system, the stability of pramipexole or its salt preparations, especially pramipexole hydrochloride oral liquid, has been significantly improved. The solution formulation formed by mixing pramipexole hydrochloride with preservative and water shows excellent stability and bioavailability, and achieves unexpected effects, thereby providing a simple and stable pramipexole hydrochloride Oral liquid. The invention perfectly realizes multi-dose administration of pramipexole hydrochloride, and provides a new administration method of pramipexole hydrochloride for the clinic, so as to effectively treat Parkinson's disease and improve the compliance and accessibility of medication for patients.

Figure 1:
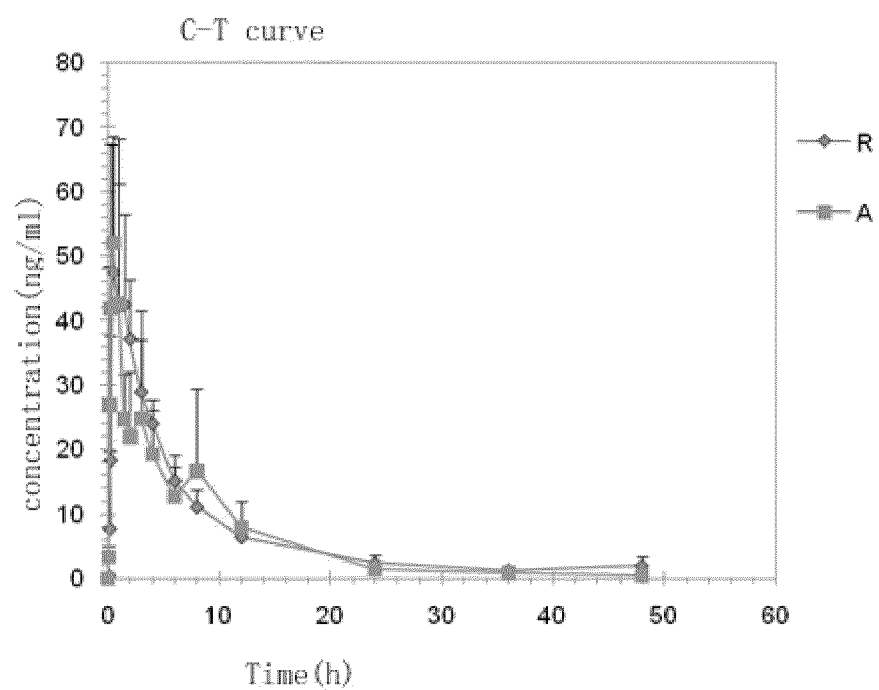
FIG. 1 is the comparison results of the bioavailability of the oral liquid of Example 2 of the present invention and that of the comparative preparation (0.25 mg pramipexole hydrochloride tablets)

Wherein R drug refers to the comparative preparation and A drug refers to the preparation of Example 2.

DETAILED DESCRIPTION OF THE PREFERRED EMBODIMENT

The present invention can be further described through the following examples, but the scope of the present invention is not limited to the following examples.

In the preparation of various compositions below, if not otherwise specified, the total volume of each batch is 10000 ml. The formula and preparation method are explained based on the composition of each 100 ml liquid medicine. When dispensing, the amount of liquid medicine in each bottle is set at 100 ml.

The detection method involved in the present invention: the detection method of related substances is determined according to high performance liquid chromatography (Chinese Pharmacopoeia 2015 Edition, Volume IV, General Requirements 0512). The stability test is carried out in accordance with the stability test as shown in Chinese Pharmacopoeia 2015 Edition, Volume IV.

Chromatographic conditions and system suitability test: Octadecylsilane bonded silica gel is used as filler (150 mm×4.6 mm, 5 µm). 9.1 g potassium dihydrogen phosphate-5.0 g sodium octane sulfonate solution (adjusted pH value to 3.0 with phosphoric acid) is used as mobile phase A. Acetonitrile-mobile phase A (1:1) is used as mobile phase B. Acetonitrile-mobile phase A (1:4) is used as solvent. The detection wavelength is 264 nm. The flow rate is 1.5 ml/min. The injection volume is 5 µl. The column temperature is 40±5° C. The gradient elution program is shown in Table 1 below:

TABLE 1

| The gradient elution program | | | | |
| --- | --- | --- | --- | --- |
| time (min) | 0 | 15 | 15.1 | 20 |
| Phase A % | 60 | 20 | 60 | 60 |
| Phase B % | 40 | 80 | 40 | 40 |

Take an appropriate amount of pramipexole hydrochloride reference substance and impurity A ((6S)-4,5,6,7-tetrahydro-1,3-benzothiazole-2,6-diamine), accurately weigh them, add the solvent to dissolve and dilute to a solution containing 7.5 µg pramipexole hydrochloride and 3.0 µg impurity A per 1 ml. The prepared solution is used as the system suitability solution. Accurately measure 5 µL of the system suitability solution and inject it into the liquid chromatograph and record the chromatogram. The resolution of impurity A and pramipexole hydrochloride must not be less than 6.0, and the pramipexole hydrochloride tailing factor must not be greater than 2.0.

Determination method: Take an appropriate amount of this product and dilute it with the solvent to a solution containing 1.5 mg of pramipexole hydrochloride per 1 ml, as the test solution. Accurately measure an appropriate amount of the test solution, add the solvent to dissolve and dilute to a solution containing pramipexole hydrochloride 1.5 µg per 1 ml, as a self-control solution. Precisely measure 5 µL each of the test solution and the self-control solution, respectively inject them into the liquid chromatograph and record the chromatogram. Calculate according to the following formula. If there are chromatographic peaks in the chromatogram of the test solution, the sum of the peak areas of each impurity must not be greater than 5 times (0.5%) of the main peak area of the self-control solution.

Impurity content % = $(r_u/r_s) * (C_s/C_u) * 100\%$ $r_u$: Peak area of each impurity in the test solution
$r_s$: Peak area of pramipexole hydrochloride in self-control solution
$C_s$: Concentration of pramipexole hydrochloride reference substance in self-control solution (mg/ml)
$C_u$: Concentration of pramipexole hydrochloride in the test solution (mg/ml)

Reference example: total impurity content of pramipexole hydrochloride tablets under light and different temperatures Sample: Take pramipexole hydrochloride tablets within the validity period (trade name: Senfalol, specification 0.25 mg) for experiment. The above methods were used to detect related substances, and the results are shown in Table 2 below:

TABLE 2

Total impurity content (%) of pramipexole hydrochloride tablets under various conditions

| Condition Time (day) | Light | 40° C. | 60° C. |
|---|---|---|---|
| 0 | 2.35 | 2.35 | 2.35 |
| 10 | 2.35 | 2.63 | 2.98 |
| 30 | 3.65 | 2.92 | 3.39 |
| 60 | 4.73 | 3.21 | 4.61 |
| 90 | 14.10 | 4.55 | 6.38 |

The results show that pramipexole hydrochloride tablets are degraded to a large extent when placed under the conditions of light, 40° C. and 60° C., and there are big problems in stability, which poses a great hidden danger to the safety of patients' medication. The conclusion of the test confirms the existing technical reports in the prior arts on the stability of pramipexole hydrochloride tablets.

Example 1: Pramipexole Hydrochloride Oral Liquid

The composition of the preparation is as follows:

TABLE 3

Composition of pramipexole hydrochloride oral liquid in Example 1

| Component | Amount (g) | Function |
|---|---|---|
| pramipexole hydrochloride | 0.0125 | medicinal ingredient |
| methyl paraben | 0.18 | preservative |
| propyl Paraben | 0.02 | preservative |
| water | 99.7875 | solvent |

Preparation: put the prescription amount of water in the preparation tank, turn on the heating, the temperature is 80° C., turn on the stirring, the speed is 400 rpm, 15 minutes later, add the prescription amount of methyl paraben and propyl paraben, and stir until dissolved. Add the prescription amount of pramipexole hydrochloride to dissolve, filter, canned, and then obtain pramipexole hydrochloride oral liquid.

The above methods were used to detect related substances, and the results are shown in Tables 4-5 respectively.

TABLE 4 pH value change of pramipexole hydrochloride oral liquid of Example 1 under various conditions

| Condition Time (day) | Room temperature | Light | 40° C. | 60° C. |
|---|---|---|---|---|
| 0 | 4.20 | 4.20 | 4.20 | 4.20 |
| 10 | 4.25 | 4.27 | 4.24 | 4.28 |
| 30 | 4.31 | 4.35 | 4.33 | 4.39 |
| 60 | 4.28 | 4.38 | 4.35 | 4.41 |
| 90 | 4.36 | 4.41 | 4.41 | 4.42 |

TABLE 5

Total impurity content (%) of pramipexole hydrochloride oral liquid of Example 1 under various conditions

| Conditon Time (day) | Room temperature | Light | 40° C. | 60° C. |
|---|---|---|---|---|
| 0 | 0.08 | 0.08 | 0.08 | 0.08 |
| 10 | 0.08 | 0.13 | 0.08 | 0.17 |
| 30 | 0.12 | 0.15 | 0.08 | 0.43 |
| 60 | 0.14 | 0.16 | 0.13 | 0.75 |
| 90 | 0.17 | 0.31 | 0.21 | 1.29 |

Example 2: Pramipexole Hydrochloride Oral Liquid

The composition of the preparation is as follows:

TABLE 6

Composition of pramipexole hydrochloride oral liquid in Example 2

| Component | Amount (g) | Function |
|---|---|---|
| pramipexole hydrochloride | 0.0125 | medicinal ingredient |
| methyl paraben | 0.18 | preservative |
| propyl paraben | 0.02 | preservative |
| EDTA-2Na | 0.025 | chelating agent |
| water | 99.7625 | solvent |

Preparation: put the prescription amount of water in the preparation tank, turn on the heating, the temperature is 80° C., turn on the stirring, the speed is 400 rpm, 15 minutes later, add the prescription amount of methyl paraben and propyl paraben, and stir until dissolved. Add the prescription amount of EDTA-2Na and pramipexole hydrochloride to dissolve, filter, canned, and then obtain pramipexole hydrochloride oral liquid.

The above methods were used to detect related substances, and the results are shown in Tables 7-8 respectively.

TABLE 7 pH value change of pramipexole hydrochloride oral liquid of Example 2 under various conditions

| Condition Time (day) | Room temperature | Light | 40° C. | 60° C. |
|---|---|---|---|---|
| 0 | 4.29 | 4.29 | 4.29 | 4.29 |
| 10 | 4.31 | 4.40 | 4.31 | 4.36 |
| 30 | 4.27 | 4.38 | 4.31 | 4.35 |
| 60 | 4.36 | 4.46 | 4.40 | 4.42 |
| 90 | 4.35 | 4.43 | 4.39 | 4.41 |

TABLE 8

Total impurity content (%) of pramipexole hydrochloride oral liquid of Example 2 under various conditions

| Condition Time (day) | Room temperature | Light | 40° C. | 60° C. |
|---|---|---|---|---|
| 0 | 0.07 | 0.07 | 0.07 | 0.07 |
| 10 | 0.07 | 0.07 | 0.09 | 0.07 |
| 30 | 0.14 | 0.16 | 0.10 | 0.15 |
| 60 | 0.15 | 0.21 | 0.15 | 0.45 |
| 90 | 0.17 | 0.28 | 0.20 | 0.96 |

Example 3: Pramipexole Hydrochloride Oral Liquid

The composition of the preparation is as follows:

TABLE 9

Composition of pramipexole hydrochloride oral liquid in Example 3

| Component | Amount (g) C1 | C2 | C3 | C4 | Function |
|---|---|---|---|---|---|
| pramipexole hydrochloride | 0.025 | 0.025 | 0.025 | 0.025 | medicinal ingredient |
| methyl paraben | 0.18 | 0.18 | 0.18 | 0.18 | preservative |
| propyl paraben | 0.02 | 0.02 | 0.02 | 0.02 | preservative |
| aminotriacetic acid | 0.025 | / | / | / | chelating agent |
| hydroxyethyl ethylenediamine triacetic acid | / | 0.025 | / | / | chelating agent |
| diethylenetriaminepentaa-cetic acid | / | / | 0.025 | / | chelating agent |
| EDTA-GaNa2 | / | / | / | 0.025 | chelating agent |
| water | 99.75 | 99.75 | 99.75 | 99.75 | solvent |

Preparation: respectively put the prescription amount of water in the preparation tank, turn on the heating, the temperature is 80° C., turn on the stirring, the speed is 400 rpm, 15 minutes later, add the prescription amount of methyl paraben and propyl paraben, and stir until dissolved. Add the prescription amount of aminotriacetic acid, hydroxyethylethylenediaminetriacetic acid, diethylenetriaminepentaacetic acid, or EDTA-GaNa2, and pramipexole hydrochloride to dissolve, filter and canned to obtain pramipex hydrochloride oral liquid.

The above methods are used to detect related substances, and the results are shown in Tables 10-13:

TABLE 10

Total impurity content (%) of pramipexole hydrochloride oral liquid of C1 in Example 3 under various conditions

| Condition Time (hour) | 40° C. | 60° C. | 80° C. |
|---|---|---|---|
| 0 | 0.07 | 0.07 | 0.07 |
| 2 | 0.07 | 0.07 | 0.08 |
| 4 | 0.07 | 0.07 | 0.08 |
| 6 | 0.07 | 0.07 | 0.07 |
| 8 | 0.08 | 0.08 | 0.08 |

TABLE 11

Total impurity content (%) of pramipexole hydrochloride oral liquid of C2 in Example 3 under various conditions

| Condition Time (hour) | 40° C. | 60° C. | 80° C. |
|---|---|---|---|
| 0 | 0.07 | 0.07 | 0.07 |
| 2 | 0.08 | 0.08 | 0.07 |
| 4 | 0.08 | 0.08 | 0.07 |
| 6 | 0.07 | 0.08 | 0.07 |
| 8 | 0.08 | 0.08 | 0.07 |

TABLE 12

Total impurity content (%) of pramipexole hydrochloride oral liquid of C3 in Example 3 under various conditions

| Condition Time (hour) | 40° C. | 60° C. | 80° C. |
|---|---|---|---|
| 0 | 0.07 | 0.07 | 0.07 |
| 2 | 0.08 | 0.08 | 0.07 |
| 4 | 0.07 | 0.07 | 0.08 |
| 6 | 0.07 | 0.08 | 0.07 |
| 8 | 0.08 | 0.08 | 0.07 |

TABLE 13

Total impurity content (%) of pramipexole hydrochloride oral liquid of C4 in Example 3 under various conditions

| Condition Time (hour) | light | 40° C. | 60° C. |
|---|---|---|---|
| 0 | 0.07 | 0.07 | 0.07 |
| 2 | 0.07 | 0.08 | 0.08 |
| 4 | 0.06 | 0.08 | 0.08 |
| 6 | 0.09 | 0.08 | 0.09 |
| 8 | 0.09 | 0.08 | 0.07 |

Comparative Example 1

The composition of the preparation is as follows:

TABLE 14

Composition of pramipexole hydrochloride oral liquid in comparative example 1

| Component | Amount C1-C2 | Amount C3-C5 | Function |
|---|---|---|---|
| pramipexole hydrochloride | 0.0125 | 0.0125 | medicinal ingredient |
| citrate | 0.6 | appropriate amount | buffer system |
| sodium citrate | appropriate amount | 1.5 | buffer system |
| methyl paraben | 0.18 | 0.18 | preservative |
| propyl Paraben | 0.02 | 0.02 | preservative |
| water | 98.7 | 98.7 | solvent |

Note: C1 pH 3.0; C2 pH 4.0; C3 pH 5.0; C4 pH 6.0; C5 pH 7.0

Preparation: respectively put the prescription amount of water in the preparation tank, turn on the heating, the temperature is 80° C., turn on the stirring, the speed is 400/min, 15 minutes later, add the prescription amount of methyl paraben and propyl paraben, and stir until dissolving, add the prescribed amounts of citric acid, sodium citrate, and pramipexole hydrochloride to dissolve, filter and canned to obtain pramipexole hydrochloride oral liquid.

The above methods were used to detect related substances, and the results are shown in Tables 15-16.

TABLE 15 pH value change of pramipexole hydrochloride oral liquid of comparative example 1 under various conditions

| Condition | pH | 0 days | 10 days | 30 days | 60 days | 90 days |
|---|---|---|---|---|---|---|
| Room temperature | 3 | 3.02 | 3.05 | 3.03 | 3.01 | 3.01 |
| | 4 | 4.00 | 4.03 | 4.05 | 4.03 | 4.08 |
| | 5 | 5.02 | 5.04 | 5.06 | 5.05 | 5.10 |
| | 6 | 6.02 | 6.04 | 6.06 | 6.05 | 6.07 |
| | 7 | 6.96 | 6.95 | 6.99 | 7.06 | 6.99 |
| Light | 3 | 3.02 | 3.02 | 3.02 | 2.99 | 2.99 |
| | 4 | 4.00 | 4.02 | 4.04 | 4.01 | 4.06 |
| | 5 | 5.02 | 5.04 | 5.07 | 5.03 | 5.11 |
| | 6 | 6.02 | 6.05 | 6.04 | 6.02 | 6.09 |
| | 7 | 6.96 | 7.00 | 7.00 | 6.96 | 7.01 |
| 40°C | 3 | 3.02 | 3.04 | 3.03 | 3.02 | 3.01 |
| | 4 | 4.00 | 4.04 | 4.05 | 4.03 | 4.07 |
| | 5 | 5.02 | 5.04 | 5.07 | 5.07 | 5.10 |
| | 6 | 6.02 | 6.06 | 6.06 | 6.05 | 6.12 |
| | 7 | 6.96 | 6.96 | 7.01 | 7.00 | 7.03 |
| 60°C | 3 | 3.02 | 3.04 | 3.08 | 3.01 | 3.01 |
| | 4 | 4.00 | 4.05 | 4.04 | 4.02 | 4.02 |
| | 5 | 5.02 | 5.05 | 5.06 | 5.04 | 5.09 |
| | 6 | 6.02 | 6.06 | 6.06 | 6.00 | 6.06 |
| | 7 | 6.96 | 6.98 | 7.05 | 7.05 | 7.04 |

TABLE 16

Total impurity content (%) of pramipexole hydrochloride oral liquid of comparative example 1 under various conditions

| Time Condition | pH | 0 days | 10 days | 30 days | 60 days | 90 days |
|---|---|---|---|---|---|---|
| Room temperature | 3 | 0.12 | 0.20 | 0.26 | 0.30 | 0.30 |
|  | 4 | 0.07 | 0.15 | 0.21 | 0.24 | 0.28 |
|  | 5 | 0.07 | 0.20 | 0.51 | 0.65 | 0.83 |
|  | 6 | 0.07 | 0.17 | 0.55 | 0.78 | 0.80 |
|  | 7 | 0.07 | 0.13 | 0.18 | 0.27 | 0.28 |
| Light | 3 | 0.12 | 5.01 | 8.09 | 9.71 | 13.50 |
|  | 4 | 0.07 | 5.67 | 8.56 | 9.49 | 9.89 |
|  | 5 | 0.07 | 4.99 | 7.15 | 7.22 | 10.54 |
|  | 6 | 0.07 | 2.73 | 4.82 | 5.62 | 5.72 |
|  | 7 | 0.07 | 0.51 | 1.72 | 2.90 | 3.82 |
| 40°C | 3 | 0.12 | 0.28 | 0.32 | 0.39 | 0.56 |
|  | 4 | 0.07 | 0.26 | 0.82 | 1.20 | 1.51 |
|  | 5 | 0.07 | 0.54 | 1.40 | 2.02 | 2.40 |
|  | 6 | 0.07 | 0.45 | 1.07 | 1.54 | 2.08 |
|  | 7 | 0.07 | 0.13 | 0.63 | 1.19 | 1.69 |
| 60°C | 3 | 0.12 | 0.72 | 1.13 | 1.64 | 2.28 |
|  | 4 | 0.07 | 1.75 | 3.24 | 5.34 | 6.92 |
|  | 5 | 0.07 | 3.32 | 5.24 | 7.45 | 8.82 |
|  | 6 | 0.07 | 1.37 | 3.05 | 4.79 | 6.70 |
|  | 7 | 0.07 | 0.48 | 1.21 | 2.22 | 3.66 |

Comparative Example 2

The composition of the preparation is as follows:

TABLE 17

Composition of pramipexole hydrochloride oral liquid in comparative example 2

| Component | Amount (g) C1-C2 | Amount (g) C3-C5 | Function |
|---|---|---|---|
| pramipexole hydrochloride | 0.0125 | 0.0125 | medicinal ingredient |
| phosphoric acid | appropriate amount | appropriate amount | buffer system |
| disodium hydrogen phosphate anhydrous | 0.2 | 0.1 | buffer system |
| methyl paraben | 0.18 | 0.18 | preservative |
| propyl Paraben | 0.02 | 0.02 | preservative |
| water | 99.7 | 99.7 | solvent |

Note: C1 pH 3.0; C2 pH 4.0; C3 pH 5.0; C4 pH 6.0; C5 pH 7.0

Preparation: respectively put the prescription amount of water in the preparation tank, turn on the heating, the temperature is 80° C., turn on the stirring, the speed is 400/min, 15 minutes later, add the prescription amount of methyl paraben and propyl paraben, and stir until dissolving, add the prescribed amounts of phosphoric acid, disodium hydrogen phosphate anhydrous, and pramipexole hydrochloride to dissolve, filter and canned to obtain pramipexole hydrochloride oral liquid.

The above methods were used to detect related substances, and the results are shown in Tables 18-19.

TABLE 18 pH value change of pramipexole hydrochloride oral liquid of comparative example 2 under various conditions

| Time Condition | pH | 0 days | 10 days | 30 days | 60 days | 90 days |
|---|---|---|---|---|---|---|
| Room temperature | 3 | 3.04 | 3.11 | 3.12 | 3.09 | 3.07 |
|  | 4 | 4.02 | 4.12 | 4.10 | 4.10 | 4.11 |
|  | 5 | 4.99 | 5.03 | 5.03 | 5.09 | 5.07 |
|  | 6 | 6.04 | 6.08 | 6.05 | 6.10 | 6.06 |
|  | 7 | 7.04 | 7.04 | 7.03 | 7.06 | 7.08 |
| Light | 3 | 3.04 | 3.11 | 3.14 | 3.07 | 3.08 |
|  | 4 | 4.02 | 4.13 | 4.15 | 4.14 | 4.11 |
|  | 5 | 4.99 | 5.05 | 5.07 | 5.13 | 5.11 |
|  | 6 | 6.04 | 6.07 | 6.08 | 6.09 | 6.10 |
|  | 7 | 7.04 | 7.03 | 7.04 | 7.06 | 7.10 |
| 40°C | 3 | 3.04 | 3.11 | 3.14 | 3.10 | 3.09 |
|  | 4 | 4.02 | 4.09 | 4.15 | 4.13 | 4.11 |
|  | 5 | 4.99 | 5.05 | 5.05 | 5.12 | 5.12 |
|  | 6 | 6.04 | 6.09 | 6.07 | 6.10 | 6.12 |
|  | 7 | 7.04 | 7.06 | 7.04 | 7.08 | 7.11 |
| 60°C | 3 | 3.04 | 3.09 | 3.14 | 3.11 | 3.11 |
|  | 4 | 4.02 | 4.09 | 4.15 | 4.16 | 4.14 |
|  | 5 | 4.99 | 5.06 | 5.04 | 5.14 | 5.12 |
|  | 6 | 6.04 | 6.08 | 6.06 | 6.11 | 6.11 |
|  | 7 | 7.04 | 7.06 | 7.03 | 7.11 | 7.09 |

TABLE 19

Total impurity content (%) of pramipexole hydrochloride oral liquid of comparative example 2 under various conditions

| Time Condition | pH | 0 days | 10 days | 30 days | 60 days | 90 days |
|---|---|---|---|---|---|---|
| Room temperature | 3 | 0.13 | 0.26 | 0.29 | 0.31 | 0.36 |
|  | 4 | 0.07 | 0.19 | 0.19 | 0.22 | 0.24 |
|  | 5 | 0.07 | 0.14 | 0.19 | 0.23 | 0.31 |
|  | 6 | 0.08 | 0.15 | 0.19 | 0.33 | 0.36 |
|  | 7 | 0.07 | 0.12 | 0.15 | 0.32 | 0.34 |
| Light | 3 | 0.13 | 0.41 | 0.65 | 0.72 | 1.05 |
|  | 4 | 0.07 | 0.39 | 0.59 | 0.90 | 0.99 |
|  | 5 | 0.07 | 0.83 | 1.19 | 1.96 | 2.37 |
|  | 6 | 0.08 | 0.45 | 0.64 | 1.56 | 2.01 |
|  | 7 | 0.07 | 0.26 | 1.29 | 2.75 | 3.05 |
| 40°C | 3 | 0.13 | 0.28 | 0.30 | 0.33 | 0.44 |
|  | 4 | 0.07 | 0.27 | 0.30 | 0.30 | 0.42 |
|  | 5 | 0.07 | 0.41 | 0.45 | 0.58 | 0.73 |
|  | 6 | 0.08 | 0.36 | 1.06 | 1.20 | 1.70 |
|  | 7 | 0.07 | 0.17 | 0.53 | 0.78 | 0.92 |
| 60°C | 3 | 0.13 | 0.37 | 0.61 | 1.07 | 1.33 |
|  | 4 | 0.07 | 0.49 | 0.66 | 1.33 | 1.68 |
|  | 5 | 0.07 | 0.74 | 1.26 | 1.94 | 2.72 |
|  | 6 | 0.08 | 1.48 | 2.53 | 3.38 | 4.71 |
|  | 7 | 0.07 | 0.96 | 1.64 | 2.84 | 3.81 |

It can be seen from the data of the Reference Example, Examples 1-3 and Comparative Examples 1-2 that the stability of the oral liquid of the present invention is better than pramipexole hydrochloride tablets or pramipexole oral liquid containing a buffer or a buffer system.

Example 4: Bioequivalence Test

The bioequivalence test was conducted with pramipexole hydrochloride oral liquid (0.125 mg/ml) prepared in Example 2, using 0.25 mg pramipexole hydrochloride tablets as a comparative preparation. It was administered to the oral cavity of Beagles (n=6) in a fasting state and allowed to swallow. Blood samples of before administration and those of after administration at 0.08 h, 0.17 h, 0.25 h, 0.5 h, 1 h, 1.5 h, 2 h, 3 h, 4 h, 6 h, 8 h, 12 h, 24 h, 36 h and 48 h were taken. The blood drug concentration was analyzed by HPLC -MS. The trend of blood drug concentration is shown in FIG. 1. The ratio of the pharmacokinetic parameters is shown in Table 20 below.

TABLE 20

The ratio of pharmacokinetic parameters (preparation of Example 2/ comparative preparation)

| Sample name | Parameter | Numerical value | 90% confidence interval (90%CI) |
|---|---|---|---|
| preparation of Example 2/ comparative preparation | Area under the curve (AUC) | 0.902 | 0.730-1.074 |

From the results in FIG. 1 and Table 20, it can be seen that the oral liquid of the present invention and the comparative preparation show bioequivalence.

What is claimed is:

1. A pramipexole hydrochloride oral liquid, characterized in being comprised of pramipexole hydrochloride, preservative and water, and the said oral liquid does not contain a buffering agent and/or a buffering agent system, wherein the said preservative is methyl paraben and propyl paraben, and the said oral liquid consists of 0.0125 parts of pramipexole hydrochloride, 0.18 parts of methyl paraben, 0.02 parts of propyl paraben and 99.7875 parts of water in parts by weight.

2. A pramipexole hydrochloride oral liquid, characterized in being comprised of pramipexole hydrochloride, preservative, chelating agent and water, and the said oral liquid does not contain a buffering agent and/or a buffering agent system, wherein the said preservative is methyl paraben and propyl paraben, the said chelating agent is disodium ethylenediaminetetraacetate, and the said oral liquid consists of 0.0125 parts of pramipexole hydrochloride, 0.18 parts of methyl paraben, 0.02 parts of propyl paraben, 0.025 parts of disodium ethylenediaminetetraacetate and 99.7625 parts of water in parts by weight.

3. A pramipexole hydrochloride oral liquid, characterized in being comprised of pramipexole hydrochloride, preservative, chelating agent and water, and the said oral liquid does not contain a buffering agent and/or a buffering agent system, wherein the said preservative is methyl paraben and propyl paraben, and the said oral liquid consists of 0.025 parts of pramipexole hydrochloride, 0.18 parts of methyl paraben, 0.02 parts of propyl paraben, 0.025 parts of chelating agent and 99.75 parts of water in parts by weight, wherein the said chelating agent comprises one member selected from a group consisting of aminotriacetic acid, hydroxyethylethylenediaminetriacetic acid, diethylenetriaminepentaacetic acid and calcium disodium ethylenediaminetetraacetate.

* * * * *